United States Patent
Milum et al.

[11] Patent Number: 6,113,854
[45] Date of Patent: *Sep. 5, 2000

[54] METHOD AND APPARATUS FOR TREATMENT OF INFECTIOUS MEDICAL WASTE

[76] Inventors: Craig Milum, 5351 E. Exeter Blvd., Phoenix, Ariz. 85018; Joseph C. Sherrill, 2360 Maple Rd., Homewood, Ill. 60430

[*] Notice: This patent issued on a continued prosecution application filed under 37 CFR 1.53(d), and is subject to the twenty year patent term provisions of 35 U.S.C. 154(a)(2).

[21] Appl. No.: 08/509,996

[22] Filed: Aug. 1, 1995

[51] Int. Cl.$^7$ .......................................... A61L 9/00

[52] U.S. Cl. ................. 422/32; 422/28; 422/37

[58] Field of Search ................ 422/28, 32, 37, 422/292, 294, 300

[56] References Cited

U.S. PATENT DOCUMENTS

| | | | |
|---|---|---|---|
| 3,149,906 | 9/1964 | Thorsen | 8/128 |
| 3,318,122 | 5/1967 | Starr et al. | 68/210 |
| 3,400,467 | 9/1968 | Drace | 34/45 |
| 3,550,169 | 12/1970 | Forse | 8/150 |
| 3,597,943 | 8/1971 | Gayring | 68/210 |
| 3,650,667 | 3/1972 | Luechauer | 8/111 |
| 3,728,074 | 4/1973 | Victor | 8/142 |
| 3,742,738 | 7/1973 | Frotriede | 68/210 |
| 4,070,876 | 1/1978 | Thompson et al. | 68/3 |
| 4,224,810 | 9/1980 | Crowell | 68/3 |
| 4,235,600 | 11/1980 | Capella et al. | 8/137 |
| 4,561,268 | 12/1985 | Southwick et al. | 68/210 |
| 4,797,128 | 1/1989 | Fowler | 8/137 |
| 4,919,998 | 4/1990 | Goad et al. | 428/265 |
| 5,003,794 | 4/1991 | Griffis | 68/3 |
| 5,024,851 | 6/1991 | Goad et al. | 427/2 |
| 5,215,816 | 6/1993 | Shibata et al. | 428/266 |
| 5,277,869 | 1/1994 | Glazer et al. | 422/32 X |
| 5,374,394 | 12/1994 | Kralovic | 422/32 X |
| 5,384,092 | 1/1995 | Sawhill et al. | 422/32 |
| 5,387,350 | 2/1995 | Mason | 422/32 X |
| 5,534,162 | 7/1996 | Adams et al. | 422/28 X |
| 5,567,385 | 10/1996 | Miller et al. | 422/28 |

FOREIGN PATENT DOCUMENTS

| | | |
|---|---|---|
| 1410806 | 10/1968 | Germany . |
| 2123103 | 5/1971 | Germany . |
| 2522116 | 11/1976 | Germany . |
| 84092684 | 3/1984 | Japan ................... F07K 07/00 |

OTHER PUBLICATIONS

Shea Position Paper, Infection Control & Hospital Epidemiology, vol. 13, No. 1, Jan. 1992, pp. 39–40, 44 & 46.

de Andrade et al., Use of *Bacillus–subtilis* Spores to Evaluate the Efficiency of Sodium Hypochlorite at Different Concentration and PH Values, vol. 24.

M. Jaklevic, Incinerator Emissions Rules Cause Dispute Over Methodology And Risk, Modern Healthcare, Feb. 13, 1995, p. 18.

*Primary Examiner*—Krisanne Thornton
*Attorney, Agent, or Firm*—Stephen T. Sullivan

[57] ABSTRACT

A method is provided for treatment of infectious medical waste. The method in a broad sense includes washing the infectious medical waste with a liquid to convert the infectious medical waste into noninfectious waste. In accordance with another aspect, a method is provided which includes a first step of wetting the infectious medical waste with a first liquid to remove loose particles and materials that are soluble in the first liquid from the infectious medical waste, and a second step of wetting the infectious medical waste with a disinfecting liquid to disinfect the infectious medical waste. An apparatus also is provided for treatment of infectious medical waste. The apparatus comprises a substantially liquid-tight volume for containing the infectious medical waste. The volume includes a first input for inputting a first liquid into the volume to wet the infectious medical waste with the first liquid and thereby remove loose particles and materials that are soluble in the first liquid from the infectious medical waste.

33 Claims, 2 Drawing Sheets

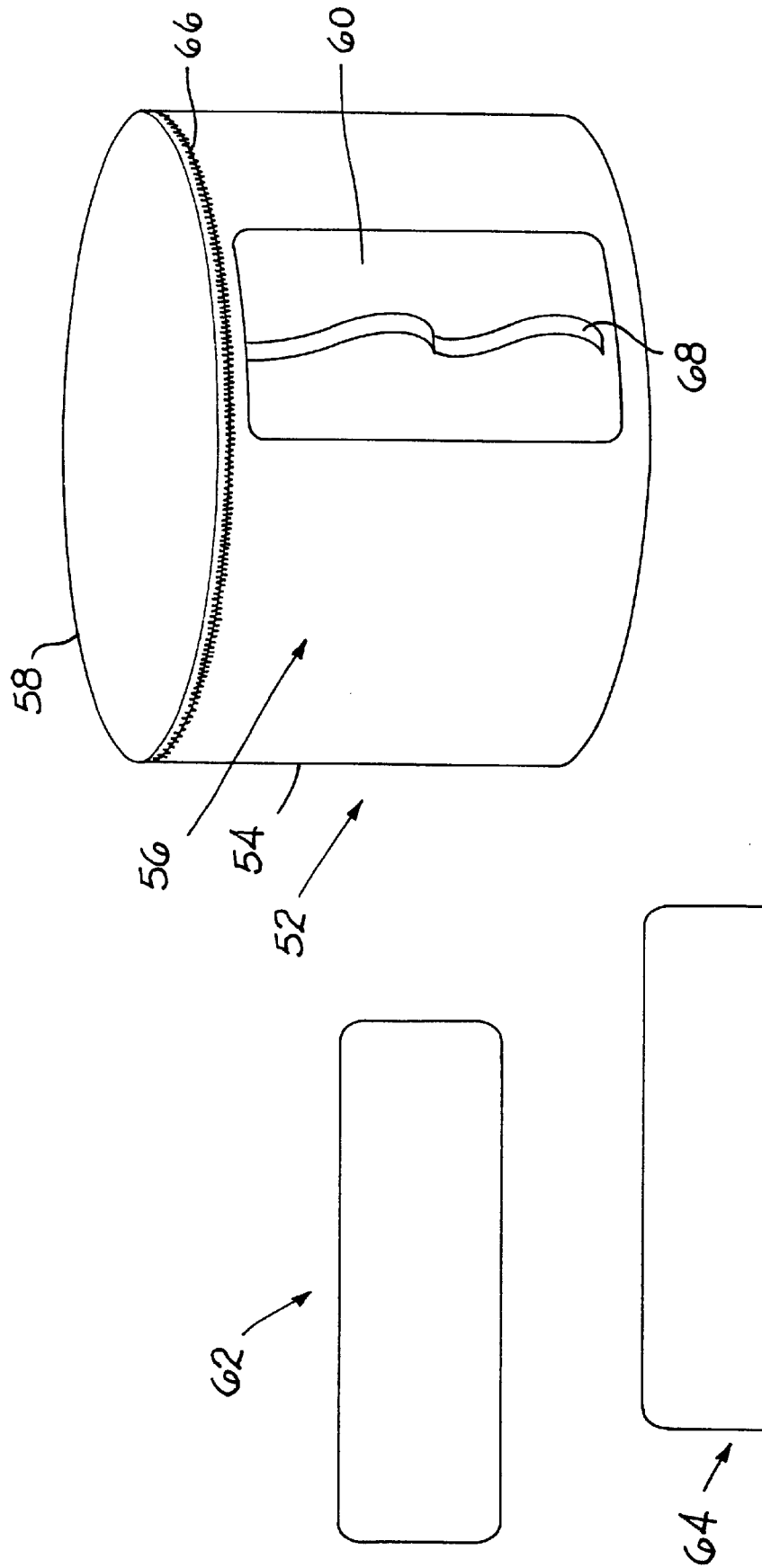

METHOD AND APPARATUS FOR TREATMENT OF INFECTIOUS MEDICAL WASTE

BACKGROUND OF THE INVENTION

1. Field of the Invention

The present invention relates to methods and apparatus for treatment of medical waste and, more specifically, to methods and apparatus for treatment of medical waste that are not dependent upon incineration.

2. Description of the Related Art

The present invention is useful for the effective treatment of a relatively wide variety of medical wastes, but its applicability and effectiveness are particularly noteworthy as to certain classes of medical wastes. There is a lack of uniformity and convention as to the use of certain terms involved in discussions of medical wastes, and for that reason some discussion of nomenclature would facilitate an understanding of the invention.

The term medical waste is defined by the U.S. Environmental Protection Agency (the "U.S. EPA") as any solid waste which is generated in the diagnosis, treatment, or immunization of human beings or animals, in research pertaining to these, or in the production or testing of a biological. 40 C.F.R. Ch.1, § 259.10(a); *U.S. Environmental Protection Agency*, Mar. 24, 1989, pp. 12,373–12,374. Biological as used herein refers to preparations made from living organisms and their products, including vaccines, cultures, etc., intended for use in diagnosing, immunizing or treating humans or animals in research pertaining thereto. Such medical waste may derive from a variety of sources, including hospitals, clinics, health maintenance organizations, and the like. Specific examples of medical wastes are provided below.

The term infectious medical waste is defined as waste containing any organism (such as a virus or bacteria) that is capable of being communicated by invasion of or multiplication in body tissues and is capable of causing disease or adverse health impacts in humans. The closely-related term regulated medical waste, used by some synonymously with the term infectious medical waste, is defined by the U.S. EPA as any solid waste [defined in 40 C.F.R. § 259.10(a)], generated in the diagnosis, treatment, (e.g., provision of medical services), or immunization of human beings or animals, in research pertaining thereto, or in the production or testing of a biological, that is not excluded or exempted under 40 C.F.R. § 259.30(b), and that is listed in the table of regulated medical waste provided at 40 C.F.R. § 259.30(a). 40 C.F.R. § 259.30 (1992).

Technically, medical waste qualifies as infectious or regulated medical waste only if it contains pathogens (microorganisms capable of causing disease) of sufficient quantity and virulence so that human exposure to the medical waste could result in infectious disease. Thus, this class of medical waste is defined in terms of its effect on humans, i.e., the effect of the waste on humans must be known or predicted to classify waste as infectious or regulated medical waste. In view of this definition, the manner in which one determines whether a particular batch of medical waste qualifies as infectious or regulated medical waste has not been reduced to a single, universally-recognized test. *Infection Control and Hospital Epidemiology*, January 1992, page 40.

One common approach to classification of such wastes involves using a subjective standard in which the waste is deemed to be infectious or regulated medical waste if it is suspected to contain pathogens in sufficient quantity and virulence to cause disease. *Infection Control and Hospital Epidemiology*, January 1992, page 39.

For purposes of the present invention, the term infectious medical waste as used hereinbelow is interpreted in a broad sense to include the U.S. EPA definition of regulated medical waste at 40 C.F.R. § 259.10(a) as referred to above, including wastes that meet the subjective standard referred to above. Moreover, the term as used in connection with the invention includes any medical waste that is handled or treated as infectious or regulated medical waste as defined by any of the above definitions.

Infectious or regulated medical waste is commonly divided into seven groups or subcategories. These subcategories, which are summarized, e.g., in the table of regulated medical waste at 40 C.F.R. § 259.30(a), include the following:

1. Cultures and Stocks

This group includes cultures from medical and pathological laboratories, cultures and stocks of infectious agents from research and industrial laboratories, wastes from the production of biologicals, discarded live and attenuated vaccines, and culture dishes and devices used to transfer, inoculate and mix cultures.

2. Pathological Wastes

This group includes tissues, organs, and body parts and body fluids that are removed during surgery or autopsy, or other medical procedures, and specimens of body fluids and their containers.

3. Human Blood and Blood Products

This group includes liquid waste human blood, products of blood, items saturated and/or dripping with human blood, or items that were saturated and/or dripping with human blood that are now caked with dried human blood, including serum, plasma, and other blood components, and their containers, which were used or intended for use in either patient care, testing and lavatory analysis, or the development of pharmaceutical. Intravenous bags are also included in this-category.

4. Sharps

This group includes sharp items that have been used in animals or human patient care or treatment or in medical research, or industrial laboratories, including hypodermic needles, syringes (with or without the attached needles), pasteur pipettes, scalpel blades, blood vials, needles with attached tubing, and culture dishes (regardless of presence of infectious agents). Also included within this group are other types of broken or unbroken glassware that were in contact with infectious agents, such as used slides and cover slips.

5. Animal Waste

This group includes contaminated animal carcasses, body parts, and bedding of animals that were known to have been exposed to infectious agents during research (including research in veterinary hospitals), production of biologicals, or testing of pharmaceutical.

6. Isolation Wastes

This group includes biological waste and discarded materials contaminated with blood, excretion, exudates or secretions from humans who are isolated to protect others from certain highly-communicable diseases, or isolated animals known to be infected with highly-communicable diseases.

7. Unused Sharps

This category includes unused discarded hypodermic needles, suture needles, syringes, and scalpel blades.

The present invention is well suited for the effective treatment of a wide variety of medical wastes. It is particularly well suited, however, and finds greatest practical advantage, in the treatment of solid or semi-solid infectious medical wastes falling within subcategories 3 and 6 above, i.e., blood and blood products, and isolation wastes. These materials typically comprise synthetic or man-made materials that contain microorganisms, biologicals, or pathogens. Medical waste falling within either of these two subcategories is referred to in this document as treatable medical waste.

Although most infectious medical wastes are generated in hospitals and other health care facilities, relatively little data are available on their specific composition. It is believed that infectious medical wastes typically include a heterogeneous mixture of materials such as plastics, dry cellulosic solids, wet cellulosic solids, and noncombustible materials such as metals. A typical mix of such materials within a batch of medical waste might include, for example, approximately 14% by weight of plastics, about 45% by weight of dry cellulosic material, approximately 18% by weight of wet cellulosic material, and approximately 20% by weight of noncombustibles. *Infection Control and Hospital Epidemiology*, January 1992, page 40. These wastes often comprise the disposable contents and packaging of single-use products, such as incontinency products, surgeon's instruments, woven towels, non-woven towels, non-woven surgical barrier drapes, non-woven surgical staff apparel, wound dressings, surgical sponges, examination instruments, plastic treatment vessels of many shapes and sizes, patient restraints, etc.

Infectious medical waste contains or is suspected of containing organisms capable of causing disease or adverse health impacts in humans. The term pathogen similarly refers to an agent, organism or microorganism that causes or is capable of causing disease. Examples of pathogens include bacteria, viruses, fungi, mycobacteria and spores. A given item of infectious medical waste typically will have many different types of pathogens on it, and the number of individual pathogenic microorganisms on the item typically will run into the billions. A principal object of the invention is to treat infectious medical waste in a manner that reduces the amount of pathogens so that the waste no longer qualifies as infectious medical waste. Given the extremely large numbers of pathogens encountered, and given the nature of their existence and destruction, measures of the reduction of pathogens in a specific population usually are expressed in statistical terms. In these statistical terms, the amount of pathogens remaining in the population typically are expressed in terms of colony forming units (CFU) per square inch. The State and Territorial Association on Alternate Treatment Technologies recommends requiring an inactivation of vegetable bacteria, fungi, lipophilic/hydrophilic viruses, parasites, and mycobacteria at a 6 log to the 10th power reduction or greater, and inactivation of *B. stearothermophilus* spores or *B. subtilis* spores at a 4 log to the 10th power reduction or greater. *Technical Assistance Manual: State Regulatory Oversight Of Medical Waste Treatment Technologies*, April, 1994, pages 8–12.

Heretofore, the conventional procedure for handling of medical wastes, and particularly for treatable medical wastes, in health care facilities has been as follows. As the medical wastes are created, e.g., in the health care facility, they are placed in red plastic bags. When the red plastic bags become filled, they are taken to a storage area at the health care facility and placed in large plastic drums, typically 44-gallon polyvinyl chloride drums. Lids are secured over the drums to limit odors and to limit vapor and air escape out of the drums. Periodically, the medical waste in the drums is permanently disposed of.

U.S. EPA regulations grant the individual states fairly broad discretion in regulating the handling and treatment of medical wastes. Generally, disposal of infectious medical wastes by dumping in a sanitary landfill without treatment is not permitted. Placing of infectious medical waste in a landfill can be punishable by severe fines and penalties.

The most widely used permanent disposal technique for medical wastes, including treatable medical wastes, is incineration. The incineration is undertaken at special incineration facilities, usually located at a site away from the generating health care facility. At periodic intervals, the medical wastes are picked up by a transporter at the health care facility and taken to the incineration facility. The contents of the drums then are inputted into an incinerator and incinerated. The medical wastes are thereby converted to solids, such as inert ash, and to stack gases that are released into the atmosphere.

The incineration process has been generally disadvantageous in that it is costly. Moreover, incineration brings to bear a host of environmental concerns, most importantly air quality concerns. The U.S. EPA has recently proposed rules pursuant to the 1990 Clean Air Act amendments that would mandate drastic reductions in medical waste incinerator emissions. 60 C.F.R. § 10654. This is expected to greatly increase the cost of incineration and further reduce its attractiveness as a viable disposal technique.

Steam sterilization of medical wastes has been used as an alternative to incineration. With this approach, the medical wastes are placed in an apparatus similar to an autoclave. In a typical steam sterilization process, the wastes are exposed to steam at approximately 250° F. for about 30 minutes.

Steam sterilization has been disadvantageous for treatment of medical wastes in that it requires relatively large and costly equipment, and in that it is expensive to operate due in large part to the substantial heating requirements. Steam sterilization also is disadvantageous in that it generally does not eliminate highly-objectionable visual evidence of the contamination.

Chemical disinfection, typically accompanied with grinding, is a process in very limited use. This treatment process grinds the wastes in a hammermill in the presence of a chemical disinfectant. This process tends to be expensive.

Thermal inactivation of solid waste, another such process, is accomplished by the application of dry heat in an oven which is usually operated by electricity. This process involves pre-shredding he waste, initially heating it typically with an electric source, and then maintaining a temperature of around 200° F. for approximately two hours in a large enclosed chamber. This process also tends to be expensive.

Irradiation exposes wastes to ultraviolet or ionizing radiation from a source such as cobalt 60 in an enclosed, shielded chamber. Disadvantages are the large initial cost of the equipment, the skilled personnel required for safe operation, and the disposal problem for the decaying radiation source. The method is only effective generally if the ultraviolet radiation reaches the pathogenic waste and there is generally little radiation penetration through the waste which tends not to be ultraviolet transparent.

OBJECTS OF THE INVENTION

Accordingly, an object of the present invention is to provide a method and apparatus for treatment of infectious medical waste that does not require incineration.

Another object of the present invention is to provide a method and apparatus for treatment of infectious medical waste that poses less of a threat to environmental quality than incineration.

Still another object of the present invention is to provide an apparatus and method for treatment of medical waste that is less costly relative to incineration.

Additional objects and advantages of the invention are set forth in the description which follows, and in part will be apparent from the description, or may be learned by practice of the invention. The objects and advantages of the invention may be realized and obtained by means of the instrumentalities and combinations pointed out in the appended claims.

SUMMARY OF THE INVENTION

To achieve the foregoing objects, and in accordance with the purposes of the invention as embodied and broadly described in this document, methods and apparatus are provided for treating infectious medical waste to substantially reduce or eliminate pathogen populations so that the treated waste no longer is infectious and may be recycled or disposed of using conventional methods.

The invention utilizes the basic principle that medical waste, and particularly infectious medical waste, may be treated as unregulated waste if such waste has been treated so that it no longer is "infectious." This departs from conventional approaches such as incineration in which the waste itself is destroyed or physically transformed to eliminate the threat.

The approach used in the method according to the invention in broad terms involves washing the infectious medical waste with a liquid to convert the infectious medical waste into noninfectious waste. This approach is somewhat similar to the manner in which reusable textiles such as clothing are laundered. The standard approach to treating soiled reusable fabrics, of course, is through laundering. The principal objectives in reusable fabric laundering techniques are to remove stains and kill pathogens while at the same time preserving the desirable physical properties of the fabric, such as tensile strength and fiber elasticity, color, size, shape, etc. The present invention takes advantage of the disinfecting features of textile laundering approaches, while adapting such approaches to the particular needs, constraints and nuances of infectious medical waste treatment.

In accordance with the invention, a method for treatment of infectious medical waste is provided which comprises washing the infectious medical waste with a liquid to convert the infectious medical waste into noninfectious waste. The liquid preferably comprises an aqueous system, and more preferably at least one of a detergent solution and a bleaching agent.

A related method according to the invention includes a first step of wetting the infectious medical waste with a first liquid to remove loose particles and materials that are soluble in the first liquid from the infectious medical waste, and a second step of wetting the infectious medical waste with a disinfecting liquid to disinfect the infectious medical waste. The first liquid preferably comprises an aqueous solution. A particularly well suited example of the first liquid would comprise a detergent solution. The effectiveness of the method may be facilitated in some applications by imparting a mechanical action to the infectious medical waste in the first liquid. The disinfecting liquid preferably comprises a bleaching agent, for example, that may include available chlorine.

In accordance with another aspect of the invention, an apparatus is provided for treatment of infectious medical waste. The apparatus includes a substantially liquid-tight volume for containing the infectious medical waste. The compartment includes a first input means for inputting a first liquid into the volume to wet the infectious medical waste with the first liquid and thereby remove loose particles and materials that are soluble in the first liquid from the infectious medical waste. The apparatus may further include a second input means for inputting a disinfecting liquid into the substantially liquid-tight volume to disinfect the infectious medical waste.

According to still another aspect of the invention, a pliable container is provided that has proven useful in containing the medical waste during treatment. The pliable container includes a wall member forming a concavity and having a perimeter, the wall member being permeable to water, a protective surface coupled to the wall member perimeter to enclose the concavity, and an access for selectively opening and closing the container.

The first and second steps of the method may be, and preferably are, carried out sequentially. This is not, however, necessary. The method may be carried out, in some instances advantageously so, by performing the first and second steps simultaneously or with some overlap.

After treatment using the methods and apparatus of the invention, the resultant uncontaminated and unregulated wastes may be discarded in the normal fashion, e.g., by disposal in a sanitary landfill. Selected items from the resultant wastes also may be retrieved for subsequent use or recycling.

BRIEF DESCRIPTION OF THE DRAWING

The accompanying drawings, which are incorporated in and constitute a part of the specification, illustrate a presently preferred embodiment and method of the invention and, together with the general description given above and the detailed description of the preferred embodiment and method given below, serve to explain the principles of the invention.

FIG. 2 shows a mesh bag in accordance with the invention. This mesh bag is useful for containing infectious medical waste during treatment according to the method of the invention.

DETAILED DESCRIPTION OF THE PREFERRED EMBODIMENTS AND METHODS

Figure 1:
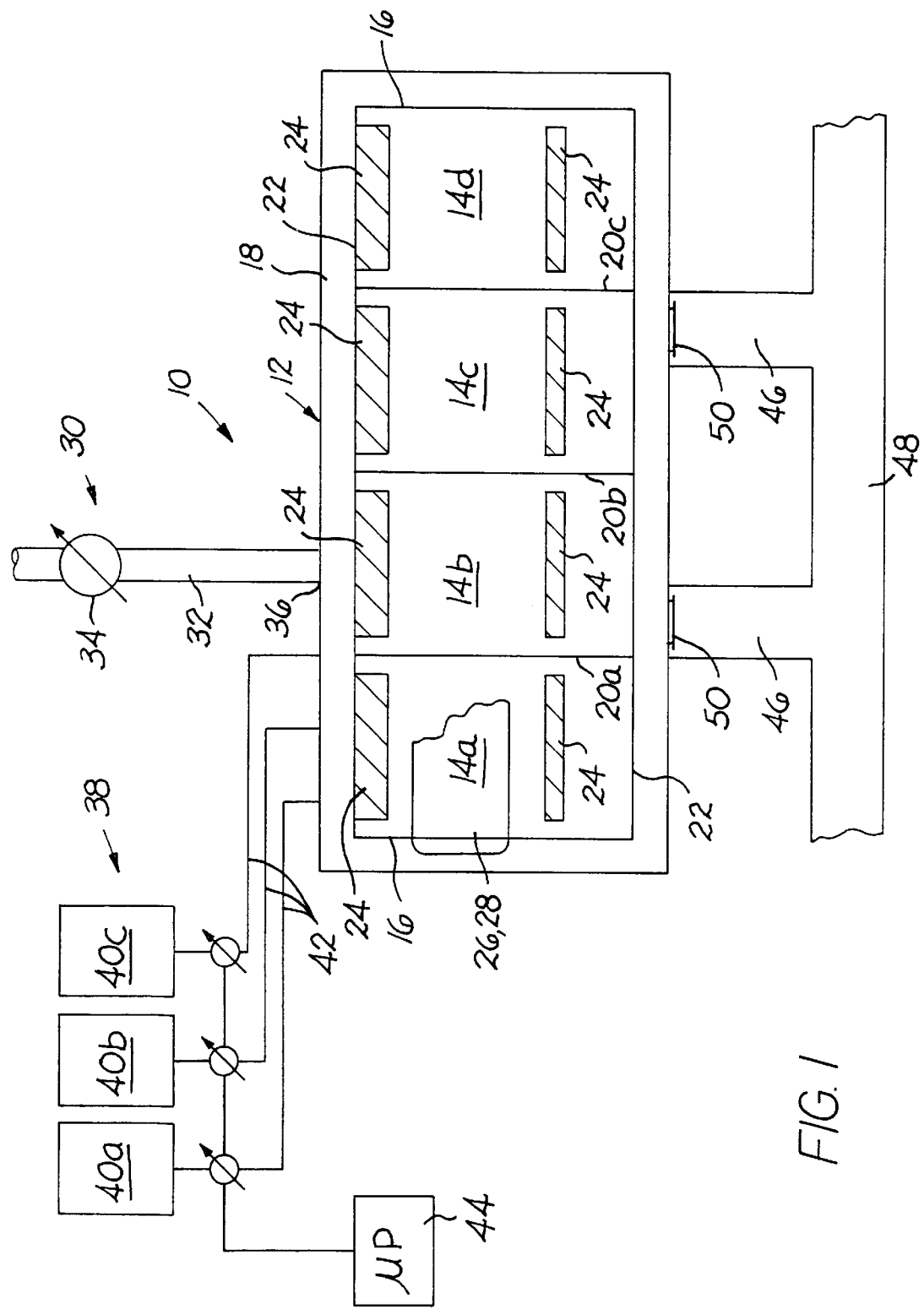
FIG. 1. shows a first preferred embodiment of the invention. This embodiment is designed for batch-type treatment of infectious medical waste.

Reference will now be made in detail to the presently preferred embodiments and methods of the invention as illustrated in the accompanying drawings, in which like reference characters designate like or corresponding parts throughout the drawings.

The preferred apparatus and methods of the invention are useful for treatment of a variety of infectious medical wastes. They are particularly attractive, however, for treatment of what has been defined herein as treatable medical waste. The apparatus and methods are useful as a general matter for infectious medical waste in which the carrier or vehicle or substrate for the pathogens is a solid or semi-solid material. The medical waste need not be impervious to the liquids or to the washing process. Paper products, which for example typically disintegrate into pulp particles easily viewable with the naked eye when subjected to water-based washing processes, typically are suitable for treatment according to the invention.

In accordance with the invention, an apparatus is provided for treatment of infectious medical waste. The apparatus in broad terms comprises a substantially liquid-tight volume for containing the infectious medical waste. A first input means is provided for inputting a first liquid into the volume to wet the infectious medical waste with the first liquid and thereby remove loose particles and materials that are soluble in the first liquid from the infectious medical waste. Preferably, the apparatus also includes a second input means for inputting a disinfecting liquid into the substantially liquid-tight volume to disinfect the infectious medical waste. The first and second input means in some embodiments may be one and the same, or they may share common or overlapping articles of hardware.

The apparatus of the invention also optionally but preferably includes means for imparting a mechanical action to the infectious medical waste, and evacuation means for evacuating bulk quantities of the first liquid from the substantially liquid-tight volume.

As a specific yet merely illustrative example, a first preferred embodiment 10 of the apparatus according to the invention is shown in FIG. 1. This embodiment comprises a commercial-scale laundering machine 12 such as an Ellis automatic unloading washer (54"×108"), marketed by Ellis Corp. of Itasca, Ill. The internal volume of the machine is approximately 144 cubic feet. Machine 12 includes four volumes in the form of four washer pockets or compartments 14a–d. Machine 12 has a rotating-drum design in which the treatment volumes or compartments comprise an axially-mounted horizontal cylinder 16 that is rotatable about the longitudinal axis of the compartments. The cylindrical compartments are contained within a rigid and substantially liquid-tight shell 18. Each of the compartments is substantially circular with an internal diameter of about 54 inches, a length of about 27 inches, and an internal volume of about 36 cubic feet. Interior walls 20a–c separate compartments 14a–d so that wall 20a is between compartments 14a and 14b, wall 20b is between compartments 14b and 14c, and so on. Each compartment has a rigid exterior wall 22 that is perforated with a relatively large number of perforations or holes of sufficient size (e.g., about 0.25 to 0.5 inches in diameter) that they are readily permeable by the liquids used in the machine in accordance with the invention. Ribs or vanes 24 are fixed on the interior walls to facilitate agitation, as explained more fully below. Each compartment has an opening or aperture 26 for inputting and removing articles such as the infectious medical wastes or containers of such wastes, as further described below. Doors 28 are provided to close shell 18 and provide a substantially liquid-tight seal.

The first input means as embodied in machine 12 comprises a water inlet system for selectively inputting water and other liquids such as detergent solutions, as described more fully below. Water inlet system includes piping 32, a water inlet valve 34, and one or more water inlets 36 into the respective compartments. Water inlet system 30 is coupled to and in fluid communication with a water source (not shown), such as a municipal water supply that provides tap water-quality water. Water inlet system 30 also is coupled to and in fluid communication with a water heating system (not shown), such as a commercially-available hot water heater or industrial heat exchanger, so that the water as it is inputted into the compartment by water inlets 36 can have a temperature, selected by an operator, of from ambient temperature to about 200° F.

Machine 12, and more specifically the first input means, also includes as a preferred option the capability to separately add components of the first liquid. For example, in many applications it is advantageous for the first liquid to include such components as alkaline components (e.g., sodium hydroxide), surfactants (surface active agents), sequestrants (e.g., water softening compounds), etc. Such components may be added directly to the water in water inlet system 30, either individually or as formulated compounds. The component adding means may take a variety of forms, depending upon the form of the additive, the specific application, the design of the machine, the treatment volume, and other factors. For additives that comprise dry supplies such as powdered detergents or for semi-solid additives such as gels, the component adding means may comprise a supply door for manual supply insertion, or a flush system in which, for example, the dry supplies are placed in a hopper and they are automatically flushed into the compartment by a liquid such as water. If the supplies are in liquid form, the component adding means may comprise a supply door through which the supplies may be poured into the compartments. Preferably, however, the component adding means would comprise a liquid feed system or automatic liquid chemical injection system in which the liquid supplies are automatically fed and inputted to the compartments at the appropriate time and in the appropriate amounts.

In the preferred embodiment, the component adding means comprises an automatic liquid chemical injection system 38 as shown in FIG. 1 which includes a plurality of supply containers 40a–c, flexible tubing 42 connected in fluid communication between supply containers 40a–c and compartments 14a–d, and a controller/regulator 44 that times, controls and regulates the flow of supplies from the respective supply containers to the compartments according to preselected settings.

Machine 12 includes means for imparting a mechanical action to the infectious medical waste. The mechanical action means may take virtually any form, provided that the effect is to impart mechanical action to the contents of the treatment compartment within the liquid contained in the compartment so that components of the waste are physically contacted and/or agitated to facilitate physical removal of pathogens from the waste. As noted above, each compartment includes a plurality of ribs or vanes 24. Shell 18 is substantially liquid-tight when doors 28 are closed and latched. A driving means such as a motor, turbine, pump, drive belt or the like (not shown) is motively coupled to cylinder 16 to selectively rotate the compartments in a desired rotational direction, at a desired speed and for a desired duration. This rotation causes the contents of the compartments, both liquid and solid, to be subjected to mechanical action. The extent of the mechanical action can be regulated, e.g., by controlling the rotational frequency of the compartments. Mechanical action also can be affected by periodically reversing the rotation of the compartments, and by regulating the frequency and speed at which the compartment rotation is reversed.

It should be noted that other mechanical action means are within the scope of the invention. For example, such means may include protrusions, blades, impellers and the like within the washer compartment, or liquid jets that spray or otherwise direct liquid into the compartments. Mechanical action also may be effected by vibrating or otherwise moving the compartment itself or having a stationary drum with a center agitator such as ones which would be found in a typical home washing machine.

An evacuation means also is provided in machine 12 for evacuating the excess or bulk quantities of liquid from the treatment volume or compartments. The evacuation means preferably comprises a drainage system that includes one or more drains 46, drainage piping 48 and a drainage valve 50. Drains 46 are disposed in shell 18 and are in fluid communication with the washer compartments 14a–d. Drainage piping 48 is coupled to and in fluid communication with drains 46, and with a discharge such as a municipal sewer system. Drainage valve 50 comprises a pneumatically-actuated valve assembly. It is disposed in the drainage piping to control the flow of liquid through the drainage system. At the appropriate time, the bulk liquid contents of the washer compartments can be drained by actuating drainage valve 50 so that bulk liquids in the compartments flow through drains 46, through drainage piping 48 and drainage valve 50, and ultimately out to the sewer system.

Machine 12 also includes a second input means for inputting a disinfecting liquid such as a bleaching agent solution into compartments 14a–d to disinfect the infectious medical waste. This second input means preferably is used after the first liquid has been inputted into the compartments. More preferably, it is used to input the disinfecting liquid after the bulk of the first liquid has been drained from the compartments.

The second input means may be separate from the first input means, it may share components with the first input means, or it may be identical to and one and the same with the first input means. Accordingly, the second input means may comprise a water inlet system as described above, a supply door or window, a supply hopper, an injector, etc. In machine 12, the second input means comprises the water inlet system 30 and automatic liquid chemical injection system 38, as described above. This second input means is in fluid communication with compartments 14a–d so that the disinfecting liquid may be injected directly into the compartments during processing.

The presently preferred method of the invention will now be described as it could be carried out using the apparatus depicted in FIG. 1. It should be noted, however, that the method of the invention is not limited to use with this machine, and may find application in many other contexts and with many other machines.

The method according to the invention may be carried out at a health care facility, at a separate site, or elsewhere. The location is not necessarily limiting. Merely for purposes of illustration, it will be assumed in this document that the method is to be carried out at a separate location, here called a treatment facility, away from the health care facilities that generated the medical waste.

As mentioned above, the medical wastes as they are obtained from the health care facilities typically comprise 44-gallon drums filled with red-bagged waste materials. These drums usually are screened at the health care facility so that only drums that are relatively clean externally and which are properly sealed with lids are transported from the health care facility to the treatment facility. Radiation monitoring also is performed at the health care facility to identify and separate any drums containing radioactive materials prior to transport.

Upon arriving at the treatment facility, the drums are moved into a receiving area, where they are visually inspected for drum integrity, leakage, sealing, visible evidence of stains or contamination, etc. Radiation monitoring may be performed here as well to screen any radioactive materials. Each drum also is weighed. After this initial processing, each drum is opened and the red bags contained in it are unloaded. Each red bag is opened and the contents are removed and inspected. Materials other than treatable infectious medical wastes are removed and placed in separate containers.

It has been learned that the batch treatment of infectious medical waste can be greatly facilitated by containing the medical waste in specially-designed containers having certain desirable properties. Accordingly, as one aspect of the invention, a pliable container or mesh bag 52 is provided which has the following construction, as illustrated in FIG. 2.

Mesh bag 52 has a generally cylindrical shape with a length of about 27 inches and a radius of about 15 inches. This provides sufficient capacity for about 35 pounds of treatable infectious medical waste. It should be noted that the shape and size of the container are not necessarily limiting. The bag shape and size may be selected, for example, to conform to the shape and size of equipment with which the bag is to be used, such as machine 12 and its compartments.

Mesh bag 52 includes a water-permeable wall member 54 forming a concavity 56 and having a perimeter 58. The wall member preferably comprises a mesh material having a mesh size of about 1/16 by 1/8 inches. The wall member may comprise, for example, a synthetic fiber mesh material with relatively low water absorptivity and reactivity, such as nylon, polyester, olefin, acrylic, modacrylic, etc. Different materials and larger or smaller mesh sizes are permissible, however, depending upon such factors as the specific medical waste being treated and the liquids being used in the treatment. The mesh size should be selected so that the wall member is permeable to water and/or other liquids that are useful in the practice of the invention, yet contains particles that might otherwise clog piping or valves, or which might exceed particle size and quantity limitations on effluent water imposed by regulation.

The container further includes a protective surface 60 coupled to wall member perimeter 58 to enclose concavity 56. The protective surface performs the important function of protecting people having access to the container from being injured by sharps or potentially injurious objects in the bag. The protective surface should have sufficient strength and impenetrability so that it will appropriately limit the risk of wounds to workers handling the bag under ordinary processing conditions and circumstances, and while processing the types of medical wastes ordinarily encountered from health care facilities.

Protective surface 60 comprises a polyvinyl chloride sheet. Alternative materials include various flexible plastic materials with high chemical resistant properties. Protective surface 60 is about 25.5 inches long, about 10 inches wide, and about 1/4 inch thick. It has an interior surface 62 and an exterior surface 64. Protective surface 60 meets and generally exceeds the criteria for strength and puncture resistance outlined above.

Mesh bag 52 includes an access in the form of a heavy-duty, corrosion-resistant zipper 66 disposed at perimeter 58 of the bag for selectively opening and closing the bag to insert and remove contents. A handle 68 is attached to exterior surface 64 of protective surface 60 to facilitate securing and moving mesh bag 52. Handle 68 comprises a woven nylon ribbon approximately 5 cm wide, approximately 1 cm thick, and running the length of protective surface 60. Handle 68 is secured to protective surface 60 by a plurality of steel rivets or other suitable means.

Returning to the description of the preferred method, after opening and inspecting the contents of the red bags, an operator places the contents of the red bags and the red bags themselves into mesh bag 52. When mesh bag 52 is substantially full, zipper 66 is zipped up to seal the bag and enclose the waste. Three mesh bags filled with infectious medical waste are placed in each of the washer compartments 14a–d of machine 12. When all washer compartments that are to be filled have been filled, doors 28 and are closed and latched.

In a broad sense, the method of the invention comprises washing the infectious medical waste with a liquid to convert the infectious medical waste into noninfectious waste. A principal objective of the method is to use liquid chemistry techniques and, more particularly, chemical laundering-type techniques, to convert infectious medical waste into benign, non-infectious waste. This requires the reduction of pathogens down to a level sufficiently close to zero in statistical terms as to be acceptable for categorization and handling as non-infectious wastes. For example, the reduction in pathogenic activity would have to be reduced so that the wastes no longer qualify as infectious medical wastes as that term is used in this document, which includes the definitions provided above. The State and Territorial Association on Alternate Treatment Technologies recommends requiring a level of disinfection demonstrated by the ability to inactivate surrogate pathogens such as vegetable bacteria, fungi, lipophilic/hydrophilic viruses, parasites, and mycobacteria at a 6 log to the 10th power reduction or greater; and to inactivate *B. stearothermophilus* spores or *B. subtilis* spores at a 4 log to the 10th power reduction or greater. *Technical Assistance Manual: State Regulatory Oversight Of Medical Waste Treatment Technologies*, April, 1994 pages 8–12. The elimination of pathogens may be through physical removal, through killing or destruction of the pathogens, etc.

In eliminating pathogens using a washing or laundering-type approach, the effectiveness of the process may be regulated or controlled by a number of liquid treatment factors, principal among which include the following: (1) chemical function of the liquid or liquids used (including composition, concentration of the various chemical species present, chemical activity, etc.), (2) temperature, (3) mechanical action, (4) time or duration of processing and of the stages of processing, if the processing is staged (e.g., rinse, detergent cycle, bleaching cycle, etc.), and (5) dilutions (e.g., number of cycles or replacements of liquid baths). Each of these liquid treatment factors includes a number of subsidiary factors, parameters and variables. In addition, there are interactions or trade-offs among the various factors.

As a general matter, aqueous systems (systems based on the use of water) usually are preferred for the treatment of infectious medical wastes in accordance with the invention. Water is a universal solvent that is widely recognized for its unique and attractive properties. In most instances, water is readily available in ample quantities and at low cost.

For most applications, the aqueous system should be mildly alkaline for the predominant portion of the treatment. The pH levels preferably will be in the range of 8 to 10. Water hardness should be avoided to limit the formation of insoluble metal salts, particularly where detergents or other surfactants are employed. The temperature of the aqueous system for most applications should be at least about 140° F., and preferably should be in the range of 180° F. to 205° F. for most applications. In addition, some mechanical action is preferred. In most applications, the mechanical action should be moderate to vigorous.

To illustrate the range of variations in the liquid treatment factors that are permissible within the scope of the invention, the following Examples 1–4 are provided. In each of these examples, the following conditions are assumed. The infectious medical waste to be treated are placed in mesh bags 52. Each bag contains approximately 35 pounds of infectious medical waste. Three of the mesh bags are placed in each of the washer compartments of machine 12, and doors 28 are secured to enclose the compartments in a substantially liquid-tight fashion.

EXAMPLE 1

Predominant Chemical Function

Water inlet is actuated to input water into compartments 14a–d. The water is tap water from a municipal water treatment source. It has an alkalinity of about 50–100 ppm as sodium bicarbonate, and a pH of about 8.0. The incoming water has been heated to a temperature of approximately 160° F. When the water level within compartments 14a–d reaches approximately 6 inches, valve 34 of water inlet system 30 closes to stop the input of water.

In this example, the liquid consists essentially of a disinfecting liquid. Accordingly, approximately 128 ounces of a 14% aqueous solution of sodium hypochlorite is added to the four compartments 14a–d through supply system 38. The aqueous system thereby created within compartments 14a–d constitutes an oxidizing bleach solution of sodium hypochlorite in which the concentration of sodium hypochlorite in which the concentration of available chlorine is about 300 ppm. The compartments of machine 12 are rotated throughout this process at a rotational frequency of about 20–30 rpm so that agitation and mechanical contacting of the contents are continuous.

Upon completion of the cycle (about 15 minutes into the process), drainage valve 50 is actuated to drain the bulk solution from the compartments. Water inlet system 30 is again actuated to input tap water for a brief rinsing cycle, this time at approximately 140° F. to 160° F. but with all other parameters for the water remaining the same. This second water input or phase is continued until the water reaches a level of approximately 6 inches. Again, agitation is continuous. The cycle is continued for approximately 3 minutes, at the completion of which drainage valve 50 is actuated to drain the bulk rinse solution from the compartments.

EXAMPLE 2

Predominant Temperature

Water inlet 34 is actuated to input water into compartments 14a–d. The water is tap water from a municipal water treatment source, as described in Example 1, above. The incoming water in this second example, however, has been heated to a temperature of approximately 200° F. The water level is the same as for Example 1. Approximately 16 ounces of detergent and non-ionic sequestrant (such as JS Concentrate, commercially-available from Industrial Blending of Queen Creek, Ariz.), 10 ounces of alkali (such as caustic soda), and 32 ounces of 14% aqueous sodium hypochlorite are added to compartments 14a–d through supply system 38. The aqueous system thereby created within compartments 14a–d constitutes a detergent and oxidizing bleach solution in which the concentration of the sodium hypochlorite is about 300 ppm. Mechanical action is employed as described in Example 1, above, as are the rinse cycle and drain procedures. The process is carried out for about 15 minutes.

EXAMPLE 3

Predominate Time Factor

This example is carried out as described for Example 1, above, but with the following modifications. The first cycle in which the waste is treated with the detergent solution is carried out for about 20 minutes. Similarly, the second cycle in which the waste is treated with a bleaching solution is carried out for about 30 minutes.

EXAMPLE 4

Time and Chemical Action Combined Predominant

In this example, a sodium hypochlorite solution of 0.1% is mixed in a large tank of water at ambient temperature. The infectious medical wastes are placed in a basket and submerged completely for a four hour period. The solution is reused until its disinfection properties decline to a point at which testing indicates that the surrogate pathogen test inactivation in the center of the medical waste load no longer meets regulatory requirements. Generally this is a function of volume of sodium hypochlorite solution in proportion to pounds of regulated medical waste processed.

Examples 1–4 illustrate the broad range of parameters that are permissible within the scope of the invention for the effective treatment of infectious medical waste. Each would be expected to yield satisfactory results within the scope of the invention. Examples 1–3 illustrate that the cleaning and disinfecting effectiveness of the processing of the regulated medical wastes is a function of time, temperature, chemical action, mechanical action, and dilution. Example 4 similarly illustrates the effects and interaction of time, temperature, chemical action and dilution. It is possible to achieve a certain level of microorganism inactivation by concurrently varying these five parameters. An increase in the intensity of one action will allow for a decrease in the intensity of one or more of the other actions. If time is increased, then chemical action may be decreased while still maintaining the same level of effectiveness. To illustrate further, Example 4 uses extremes in time and chemical action in order to eliminate the need for elevated temperature, mechanical action, and dilution. The interaction of the parameters is similar but different to their interaction in textile laundering. For example, the importance of mechanical action is significantly less with infectious medical waste processing than with textile laundering. The chemical action in medical waste processing also can be used to provide benefits which linger after the process has ended. The residual coating of sodium hypochlorite left on the medical waste materials after processing is complete continues to have disinfecting benefits. These examples or variants of the key parameters may be ideally suited for a particular infectious medical waste treatment application. In the most typical cases, however, the predominance of one or two factors, as was designed into Examples 1–4, would be non-ideal. For example, the cost of chemicals in Example 1 generally would be unnecessarily high. Similarly, the cost associated with creating the elevated temperature in Example 2 would be unduly high. The cost in terms of operating capacity reductions for Example 4 also would be unnecessarily high for most applications. Therefore, a balance is preferable.

The preferred method of the invention uses a two-stage approach. According to the preferred method, the infectious medical waste is first wetted with a first liquid to remove loose particles and water-soluble materials from the infectious medical waste. This wetting most advantageously involves immersing or saturating the infectious materials with the first liquid. In the preferred method, this is accomplished by washing the waste materials during an initial wash cycle of machine 12.

As described previously, infectious medical waste is placed in each of 12 mesh bags so that each mesh bag contains approximately 35 lbs. of the waste. Three of the mesh bags are placed in each of the four washer compartments 14a–d in machine 12. Doors 28 are secured to enclose the compartments in liquid-type fashion.

Water inlet valve 34 is actuated to input tap water (as described in Example 1) into the compartments. The water has a temperature of about 140° F. to 170° F., preferably 170° F. with the other parameters for the water being as described in Example 1, above. When the water level reaches about 6 inches, the water input procedure is stopped.

The first liquid of this preferred method comprises an aqueous alkaline detergent solution. Accordingly, at this stage a detergent is added to each of the compartments.

The invention is well suited for use with a variety of alkaline detergent solutions. For example, suitable alkalies include caustic soda, soda ash, sodium orthosilicate, sodium metasilicate, and their equivalent potassium counterparts. Suitable detergent or surfactant components include commercially-available detergents, synthetic detergents, soaps, anionic and nonionic surfactants, the latter having sufficient ethoxylation to provide a cloud point of about 60° C. and 38° C. to 42° C. titre tallow soap, as surfactants; and sodium tripolyphosphate and tetrasodium pyrophosphate, or such chelating agents as disodium dihydride ethylenediamine tetraacetic acid as sequestrants. In most medical waste treatment applications, the alkaline detergent solution should have a detergent concentration sufficient to saponify or emulsify the range of fat-based soils found in infectious medical waste. Preferably, the detergent solution has a detergent concentration of about 500 parts per million (ppm) to 1,000 ppm. A suitable detergent solution may comprise sodium oxide with a concentration of at least about 250 ppm, and a surfactant with a concentration of at least about 250 ppm. The first liquid preferably has a pH of about 10.5 to 12 and an alkalinity of about 250 ppm to 1,000 ppm as sodium oxide.

The detergent composition for use in the preferred method comprises an aqueous solution of three components. These components and their approximate proportions expressed in mass percent are as follows:

| | |
|---|---|
| 1. tetrasodium ethylenediamine tetraacetate | 2.5% |
| 2. tinopal CBS-X | 0.4% |
| 3. nonylphenoxy polyethoxy ethanol (9–10 mole ethylene oxide) | 25% |

The remainder consists essentially of water. The detergent component is made by disolving the tetrasodium ethylenediamine tetraacetate and the tinopal CBS-X in water at about 100° F., then adding the nonylphenoxy polyethoxy ethanol, and finally top off the solution to the desired mass with water. For example, to make a 100 pound batch of the detergent component, 25 pounds of tetrasodium ethylenediamine tetraacetate and 0.4 pounds of tinopal CBS-X are added to water at about 100° F. while mixing. After these ingredients have dissolved, 25 pounds of nonylphenoxy polyethoxy ethanol is added while mixing. When all components have dissolved, water is added to the solution until the total weight reaches 100 pounds.

In this preferred method, 50 fluid ounces of an alkaline detergent made in this fashion is added to compartments 14a–d through liquid supply system 38. This yields a first liquid in the form of an aqueous alkaline detergent solution with a detergent concentration of about 0.04 to 0.06 mass percent (the remainder being water), a pH of about 10.5 to 11.0, an alkalinity of about 0.02 to 0.03 percent sodium oxide, and a temperature of slightly less than the water input temperature. The agitation means of machine 12 is operated continuously so that the contents of compartments 14a–d are moderately agitated. Agitation is accomplished throughout the rotation of the horizontal washer cylinder. As the cylinder turns the materials are lifted up and out of the water. The rotation speed is controlled so that a portion of the load is lifted to a point near the top of the cylinder, then allowed to drop back into the cleaning (and/or disinfecting) solution. This lifting and dropping action forces washing solution into and through all areas of the medical waste being processed.

During this agitation procedure, the detergent solution removes loose particles and water soluble materials from the infectious medical waste. The action is one of sequestering metallic salts in water and waste, saponifying and emulsifying greases and oils, and suspending them so that they can be removed by rinsing.

Upon completion of the first cycle, which takes about 10.5 minutes to complete, drainage valve 50 opens to discharge the bulk alkaline detergent solution from compartments 14a–d. When the flow rate of the alkaline detergent solution from the compartment and through drains 46 has dropped essentially to zero, drainage valve 50 is closed. At this stage, a certain amount of alkaline detergent solution remains in the medical waste within the compartments. For example, cellulosic materials typically retain moisture. The dry weight of the medical waste originally placed in the compartment may have been 400 pounds, whereas the weight of the medical waste in the compartment after drainage, and including the residual alkaline detergent solution remaining with the waste, may be over 1000 pounds.

Typically during this first alkaline detergent treatment step, approximately 90% of the pathogens are removed from the waste by detergency, by solubilizing water-soluble materials into the solution, and by physically carrying such particles and matter away from the waste materials. These removed pathogens are carried away with the bulk portion of the solution that is drained from the compartment.

The preferred method further includes a second step of wetting the infectious medical waste with a disinfecting liquid to disinfect the infectious medical waste. This second step preferably, but not necessarily, is carried out upon completion of the first step as described above. In this second step, the second input means inputs the liquid disinfectant as a bleaching agent solution, and preferably an aqueous bleaching agent solution. The substantial removal of soils in the first step and the continual break up and dissolution of the fats and oils in the second step wash water prevents in the main the chlorine from creating chlorinated organics as the sodium hypochlorite enters the process in the second step.

A number of disinfecting liquids may be employed in the practice of the invention. For example, the disinfecting liquid may comprise bleaching agents, alcohols (e.g., ethanol), peroxides, and persulfates such as potassium persulfates.

Bleaching agents often are segregated into two classes—oxidizing bleaching agents and reducing bleaching agents—and both are amenable to use in practicing the invention. Examples of suitable oxidizing bleaching agents include sodium hypochlorite and hydrogen peroxide. The oxidizing bleaching agent may be used alone or, more preferably, may be used in solution. Solvents useful in such bleaching agent solutions include water. As a general rule of thumb, the bleach concentration in the solution preferably ranges from 100 to 500 ppm on a solution basis. The disinfecting liquid preferably will have a pH of about 8 to 10.

In the preferred method of the invention, the liquid disinfectant comprises an aqueous solution of sodium hypochlorite. Superior results have been obtained where the sodium hypochlorite that is added to the water is a 12% to 14% by mass aqueous solution. Approximately 64 fl. oz. of the 12% to 14% sodium hypochlorite is added to compartments 14a–d through liquid supply system 38 to yield an available concentration in the compartments of about 340–350 ppm. The resulting aqueous sodium hypochlorite mixture has a pH of about 8–10, and a temperature in the range of 155 to 165° F. All throughout this second cycle, which lasts for about 10.5 minutes, the machine agitates to impart mechanical action to the materials in the compartment, as described above. Upon the completion of the second cycle, drainage valve 50 opens to drain the aqueous sodium hypochlorite solution from the compartments.

After the bulk liquid has been drained from the compartments, doors 28 are opened and the mesh bags are removed from the compartments by gravity as machine 12 raises and turns its opened doorways down towards a large container. The mesh bags and their contents are raised by an overhead hoist (not shown) and placed in an extractor (also not shown), and an extraction process carried out to substantially reduce the moisture content in the waste materials. As an example, the mesh bags might be centrifuged in a commercially-available extractor such as an Ellis Economizer centrifugal extractor, marketed by Ellis Corporation, Itasca, Ill. The extractor would operate at about 750 revolutions per minute (rpm) for about 5 minutes, which would be expected to reduce the liquid content of the waste to a water retention by weight of about 35% of the dry waste material weight.

After the extraction process, the mesh bags may be opened and their contents removed. The mesh bags have been cleaned and disinfected in the process, and are therefore ready for additional rounds of use and reuse. Having thus been disinfected, the waste materials removed from the mesh bags, which at the beginning of the treatment process constituted infectious medical waste, now constitute sanitized, unregulated waste that may be disposed of in a sanitary land fill. This treatment process yields waste that does not have objectionable physical appearance.

The presently preferred apparatus and method of the invention involve batch-type processing in which the infectious medical waste is treated one batch, or one group of batches, at a time. It should be appreciated, however, that the invention is quite well suited to other types of operations. For example, the invention could be advantageously employed using continuous or semi-continuous treatment operations. As an example of a semi-continuous operation, a machine such as a tunnel washing machine could be used to treat multiple batches of infectious medical waste. Operations based on washer-extractor machine designs also are useable to practice the invention. Continuous flow systems that use tunnel conveyors and the like also could be useful for the practice of the invention. Batch-type operations involving immersion or immersion baths, such as that described in Example 4 above, also are amenable.

Having now described the invention and its preferred embodiments and methods, additional advantages and modifications will readily occur to those skilled in the art. For example, the number of cycles is not necessarily limiting. Greater numbers of cycles than those disclosed above certainly could be used. The duration of treatment also is not necessarily limiting. Depending upon the circumstances, it may be advantageous to treat a given batch of mechanical waste, e.g., for one, two, four, 24 hours, or even longer. Therefore, the invention in its broader aspects is not limited to the specific details, representative devices, and illustrative examples shown and described. Accordingly, departures may be made from such details without departing from the spirit or scope of the general inventive concept as defined by the appended claims and their equivalents.

What is claimed is:

1. A method for treatment of infectious medical waste containing pathogens on waste materials, the infectious medical waste not consisting of textile items intended for reuse, the method comprising washing the infectious medical waste with a liquid comprising at least one of a detergent solution and a surfactant solution in a machine comprising a substantially liquid tight shell and a rotating drum rotatably disposed in the shell, containing and mechanically agitating the infectious medical waste in the liquid by rotating the drum to remove the pathogens from the waste materials, and separating the liquid from the waste materials to convert the infectious medical waste into noninfectious waste in the form of the separated waste materials without communition of the infectious medical waste.

2. A method as recited in claim 1, wherein the liquid comprises an aqueous system.

3. A method as recited in claim 1, wherein the liquid is at a temperature of at least about 140° F.

4. A method as recited in claim 1, wherein the liquid is at a temperature of at least about 180° F. to 205° F.

5. A method as recited in claim 1, wherein the liquid comprises a detergent solution.

6. A method as recited in claim 1, wherein the liquid comprises a disinfecting liquid.

7. A method as recited in claim 1, wherein the liquid comprises a bleaching agent.

8. A method for treatment of infectious medical waste containing pathogens on waste materials, the infectious medical waste not consisting of textile items intended for reuse, the method comprising:

a first step of washing the infectious medical waste with a first liquid comprising at least one of a detergent solution and a surfactant solution in a machine comprising a substantially liquid tight shell and a rotating drum rotatably disposed in the shell by rotating the drum to remove the pathogens from the waste materials;

a second step of removing a portion of the first liquid from the machine; and a third step performed after substantial completion of the second step of wetting the infectious medical waste with a disinfecting liquid to disinfect the infectious medical waste;

wherein the first step includes using at least one vane disposed on the rotating drum to impart mechanical action to the infectious medical waste without communition of the infectious medical waste.

9. A method as recited in claim 8, wherein the first and third steps are performed sequentially.

10. A method as recited in claim 8, wherein the first liquid comprises an aqueous solution.

11. A method as recited in claim 8, wherein the first liquid comprises a detergent solution.

12. A method as recited in claim 11, wherein the detergent solution comprises sodium oxide with a concentration of at least about 250 ppm, and a surfactant with a concentration of at least about 250 ppm.

13. A method as recited in claim 11, wherein the first liquid has a detergent concentration of about 500 ppm to 1,000 ppm.

14. A method as recited in claim 8, wherein the first liquid has a pH of about 10.5 to 12.

15. A method as recited in claim 8, wherein the first liquid has an alkalinity of about 250 ppm to 1,000 ppm as sodium oxide.

16. A method as recited in claim 8, wherein the first step includes imparting the mechanical action to the infectious medical waste in the first liquid by rotating the drum in a first direction and subsequently rotating the drum in a second direction different from the first direction.

17. A method as recited in claim 8, wherein the first step includes placing the infectious medical waste in a plurality of compartments within the drum.

18. A method as recited in claim 8, wherein the rotating drum comprises a cylindrical compartment of a textile laundering machine.

19. A method as recited in claim 8, wherein the disinfecting liquid comprises a bleaching agent.

20. A method as recited in claim 8, wherein the disinfecting liquid comprises available chlorine.

21. A method as recited in claim 8, wherein the disinfecting liquid has a pH of about 8 to 10.

22. A method as recited in claim 8, wherein the second step includes imparting a mechanical action to the infectious medical waste in the disinfecting liquid.

23. A method as recited in claim 8, further including placing the infectious medical waste in a pliable container to contain the infectious medical waste during the wetting of the first and second steps, the pliable container being permeable to the first liquid and to the disinfecting liquid.

24. A method as recited in claim 1, wherein the washing step is carried out in a textile laundering machine.

25. A method as recited in claim 1, wherein the mechanical agitation comprises agitation by horizontal rotation.

26. A method as recited in claim 1, wherein at least one vane is used to cause the mechanical agitation.

27. A method as recited in claim 1, wherein the infectious medical waste is contained within a substantially-horizontal cylindrical compartment having a horizontal longitudinal axis, and the mechanical agitation is caused at least in part by rotation of the compartment about the horizontal longitudinal axis.

28. A method as recited in claim 1, wherein the mechanical agitation comprises rotating the drum in a first direction and subsequently rotating the drum in a second direction different from the first direction.

29. A method as recited in claim 8, wherein a plurality of vanes are used to cause the mechanical action.

30. A method as recited in claim 8, wherein the infectious medical waste is contained within a substantially-horizontal compartment within the drum, and the mechanical action is caused at least in part by rotation of the compartment.

31. A method for treatment of infectious medical waste containing pathogens on waste materials, the infectious medical waste not consisting of textile items intended for reuse, the method comprising washing the infectious medical waste with a liquid comprising an aqueous detergent solution in a textile laundering machine comprising a substantially liquid-tight horizontally disposed cylindrical shell and a rotating drum rotatably disposed in the shell wherein the drum includes at least one vane, and mechanically agitating the infectious medical waste in the liquid using the at least one vane to remove the pathogens from the waste materials, and separating the liquid from the waste materials to convert the infectious medical waste into noninfectious waste in the form of the separated waste materials without communition of the infectious medical waste.

32. A method for treatment of treatable infectious medical waste containing pathogens on waste materials, the infectious medical waste not consisting of textile items intended for reuse, the method comprising washing the treatable infectious medical waste with a liquid comprising a detergent solution in a machine comprising a substantially liquid tight shell and a rotating drum rotatably disposed in the shell, and mechanically agitating the treatable infectious medical waste in the liquid by rotating the drum to remove the pathogens from the waste materials, and separating the liquid from the waste materials to convert the treatable infectious medical waste into noninfectious waste without communition of the treatable infectious medical waste.

33. A method for treatment of treatable infectious medical waste containing pathogens on waste materials, the infectious medical waste not consisting of textile items intended for reuse, the method comprising:
- a first step of washing the treatable infectious medical waste with a first liquid comprising a detergent solution in a machine comprising a substantially liquid tight shell and a rotating drum rotatably disposed in the shell by rotating the drum to remove the pathogens from the waste materials;
- a second step performed after substantial completion of removing a portion of the first liquid from the machine; and
- a third step performed after substantial completion of the second step of wetting the treatable infectious medical waste with a disinfecting liquid to disinfect the treatable infectious medical waste;
- wherein the first step includes imparting mechanical action to the treatable infectious medical waste without communition of the treatable infectious medical waste.

* * * * *